Aug. 27, 1974 R. S. MOORE Plant Pat. 3,601
MINIATURE ROSE PLANT
Filed April 23, 1973
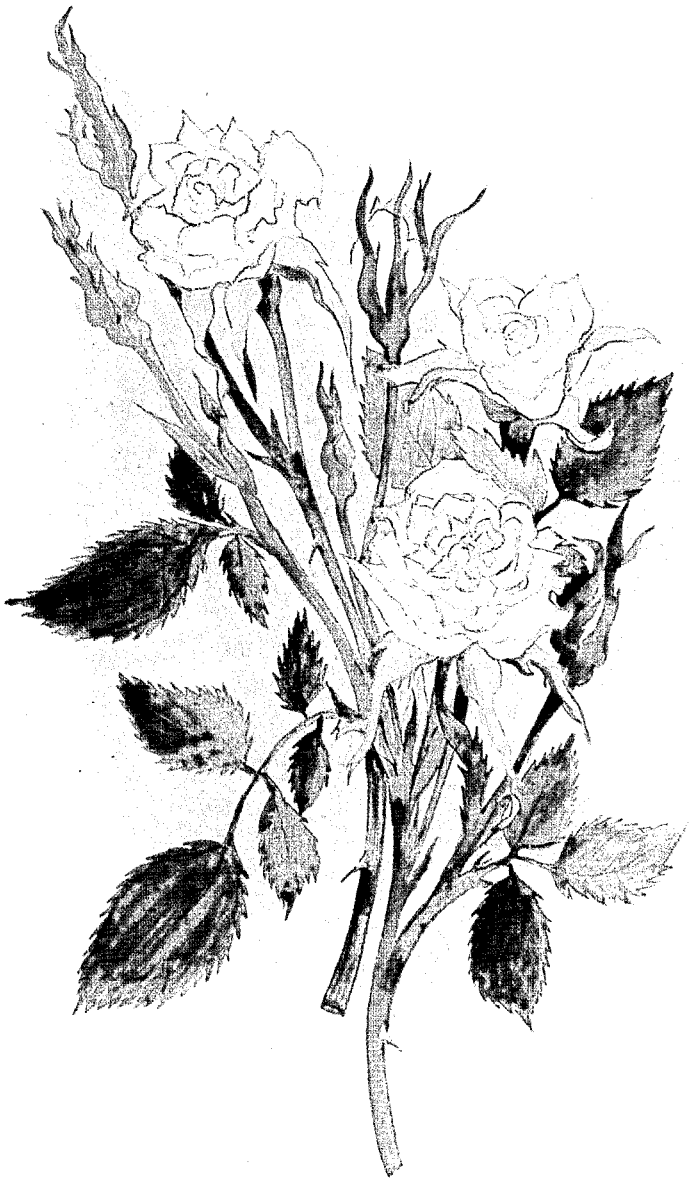

United States Patent Office

Plant Pat. 3,601

Patented Aug. 27, 1974

3,601

MINIATURE ROSE PLANT

Ralph S. Moore, 2519 E. Noble Ave., Visalia, Calif. 93277

Filed Apr. 23, 1973, Ser. No. 353,776
Int. Cl. A01h 5/00
U.S. Cl. Plt.—7 1 Claim The present invention relates to a new and distinct variety of hardy, dwarf, bush type rose plant of the miniature class; the variety being primarily characterized—as to novelty—by bi-colored buds and flowers, basically white with red to pink edges, the red coloring often blending into the white area on the upper surface of the petals but remaining essentially white with narrow red, or pink, margin on the reverse side.

The variety is further characterized by:

An abundance of bloom with flowers borne singly or in loose clusters of three or more to the stem. A plant which is more vigorous than Toy Clown (Plant Pat. 2,909) of rounded, bushy habit, with glossy, medium green leaves. The plant which has a normal average height of about 12–18" at maturity, resembles the general plant habit of Janna (Plant Pat. 3,245) miniature rose; the bud and flower being similar in form and color to Toy Clown but having more petals which are more symmetrically arranged.

A plant which grows and blooms satisfactorily both in the greenhouse and outdoors; is a good plant for growing in pots; and provides excellent garden decoration as well as cut flowers.

The present variety of miniature rose was originated by me in my nursery, located at Visalia, Calif., under conditions of careful control and observation, as a cross between Little Darling (a floribunda rose, Plant Pat 1,581) as the seed parent and Westmont (Plant Pat. 1,950) as the pollen parent.

Subsequent to origination of the variety I successfully asexually reproduced it, in my nursery located as aforesaid, by budding as well as by cuttings; the reproductions having run true in all respects.

The figure of the illustration shows a spray, including foliage, buds and flowers.

Referring now specifically to the new and distinct variety of miniature rose plant, the following is a detailed description thereof in outline; all major color plate identifications being by reference to the British Colour Council Horticultural Colour Chart, except where common terms of color definition are employed.

Type: Hardy; dwarf; bush; seedling; greenhouse; outdoors; cut flowers; garden decoration; potted plant.

Class: Miniature.

Flowers: Continuity—continuous.

*Frangrance.*—Some fragrance.

Flowers borne: Singly and several together (3 to 5) on rather stiff, wire-like, medium length stems.

Quantity of bloom: Moderate to abundant both outside and in greenhouse.

Bud: Peduncle—medium length; slender; erect; light to medium green; few very short hairs.

*Before calyx breaks.* — Size—small. Form — long, pointed; with few to several small foliaceous appendages on surface of buds and foliaceous parts extending beyond the tips of the bud equal to one-half or more of its length.

*Color.*—Medium green (in greenhouse). As calyx breaks; color red at tip, shading pinkish white (or near white), then to cream or greenish white at base.

*Size.*—Small.

*Form.*—Medium long, with petals unfurling in classic hybrid tea rose style.

*Opening.*—Opens well in all weather.

Bloom: Size when fully open: small, 1½".

*Petalage.*—Double 25–40 petals, arranged regularly.

*Form.*—Cupped, with outer petals slightly reflexed.

Petals: Rather thick; stiff, satiny both inside and outside.

Shape: Outside petals broad lanceolate with small acute tip; intermediate—broad lanceolate with acute tip; inside—lanceolate to broad lanceolate with acute tip.

Color: Newly opened flower from plant grown indoors (April 1973), Visalia, Calif.

*Outside petal.*—Outside surface—white or near white on entire surface with narrow edge or tip of Tyrian Rose 24/2; inside surface—white or near white with edge or border of Tyrian Rose 24 to 24/1 and with the outer ¼ to ⅓ (tip end) shaded in varying dilutions of the Tyrian Rose 24 color.

*Intermediate petals.*—Outside surface — same as above; inside surface—same as above.

*Inside petal.*—Outside surface—same as above; inside surface—same as above.

*General color effect newly opened flower.*—White with petal edges colored a bright contrasting shade of red or deep pink.

*Three days open.*—Essentially same effect but lighter color.

Behaviour: Spent blooms may persist for a time before petals fall.

Flower longevity (April—1973) bush or pot, 5–8 days or longer; outdoors (summer 4–6 days, in cooler spring or fall weather 6–10 days). Cut flowers at living room temperature 4–7 days.

Reproductive organs:

*Stamens.*—Moderate to abundant; arranged regularly about pistil.

*Filaments.*—Medium long; nearly white.

*Anthers.*—Yellow; well-formed.

*Pollen.*—Moderate amount.

*Pistils.*—Short to average length and number.

*Styles.*—Medium length; bunched; reddish.

*Stigma.*—Yellowish white.

*Ovaries.*—All enclosed in calyx.

*Hips.*—Few.

*Sepals.*—Permanent; spear shaped, usually two smooth and three with foliar parts along edges.

*Seeds.*—Few—usually none.

Foliage: Leaves—compound of five leaflets (occasionally 3); abundant; small, leathery, glossy.

*Leaflets.*—Shape: lanceolate, nearly oval; apex acute; base less acute; margin serrate. Color: medium to dark green; new growth often tinted bronze or reddish.

*Rachis.*—Medium strength; upper side grooved; under side sparsely thorny. Stipules: relatively narrow, medium length; short points, turning out at angle of about 45 degrees.

Growth:

*Habit.*—Dwarf; bushy; rounded; much branched.

*Growth.*—Vigorous.

*Canes.*—Medium, slender.

*Main stems.*—Color: medium green. Thorns; sparse; slender; medium length; hooked slightly downward with sharp points; color—light to medium brown. Prickles—none. Hairs—none.

*Branches.*—Color: Medium green. Thorns: sparse; medium length; hooked slightly downward; sharp needle-like points; medium length oval base. Prickles—none. Hairs—none.

*New shoots.*—Color: Medium green (often tinted bronze). Thorns; few; slender; hooked slightly downward; sharp points; base oval; color reddish-brown. Prickles—none. Hairs—none.

The miniature rose plant and its flowers as herein described may vary in slight detail due to climatic, soil and cultural conditions under which the variety may be grown; the present description being of the variety as grown at Visalia, Calif.

The following is claimed:

1. A new and distinct variety of miniature rose plant of hardy, dwarf, rounded, much branched, bush type, as illustrated and described characterized by buds and flowers resembling the Toy Clown miniature rose (Plant Pat. 2,909) in general form but with more petals and of a unique red and white color combination, resembling also in this respect Toy Clown miniature rose, the general color effect of the freshly opened flower being white with all petals edged red or deep pink (the colors tending to be more sharply contrasting than in Toy Clown) and further characterized by a plant of modest yet vigorous and compact growth, easy to propagate from hardwood and softwood cuttings, with small dark green glossy foliage, an abundance of bloom borne almost continuously throughout the growing season with flowers borne singly and in loose clusters.

No references cited.

ROBERT E. BAGWILL, Primary Examiner